United States Patent
Bohl

(10) Patent No.: US 11,389,147 B2
(45) Date of Patent: Jul. 19, 2022

(54) TABLE MOUNTED RETRACTOR SYSTEM

(71) Applicant: Dignity Health, San Francisco, CA (US)

(72) Inventor: Michael Bohl, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 23 days.

(21) Appl. No.: 17/042,655

(22) PCT Filed: Apr. 12, 2019

(86) PCT No.: PCT/US2019/027341
§ 371 (c)(1),
(2) Date: Sep. 28, 2020

(87) PCT Pub. No.: WO2019/200330
PCT Pub. Date: Oct. 17, 2019

(65) Prior Publication Data
US 2021/0030409 A1 Feb. 4, 2021

Related U.S. Application Data

(60) Provisional application No. 62/656,422, filed on Apr. 12, 2018.

(51) Int. Cl.
*A61B 17/02* (2006.01)
*A61G 13/10* (2006.01)
*A61B 17/00* (2006.01)

(52) U.S. Cl.
CPC ........ *A61B 17/0206* (2013.01); *A61G 13/101* (2013.01); *A61B 2017/00991* (2013.01); *A61B 2017/0287* (2013.01)

(58) Field of Classification Search
CPC ...... A61B 17/0206; A61B 2017/00991; A61B 2017/0287; A61B 17/02
USPC .................................................. 600/201–245
See application file for complete search history.

(56) References Cited

U.S. PATENT DOCUMENTS

| | | | | |
|---|---|---|---|---|
| 3,572,326 A | * | 3/1971 | Jensen | A61B 17/0293 600/233 |
| 3,643,655 A | * | 2/1972 | Peronti | A61B 17/02 600/228 |
| 6,488,621 B1 | * | 12/2002 | Rullo | A61B 17/02 248/558 |
| 2005/0027171 A1 | * | 2/2005 | LeVahn | A61B 17/0293 600/227 |
| 2007/0232864 A1 | * | 10/2007 | Sharp | A61B 17/0293 600/227 |

(Continued)

*Primary Examiner* — Eduardo C Robert
*Assistant Examiner* — Tara Rose E Carter
(74) *Attorney, Agent, or Firm* — Polsinelli PC

(57) ABSTRACT

The present disclosure generally relates to a table-mounted retractor system for open-spine surgery. The table-mounted retractor system includes a frame, wherein the frame is situated lateral to the patient. The table-mounted retractor system further comprises a plurality of retractor hooks wherein each of the plurality of retractor hooks are in operative association with one of a plurality of tension lines, wherein each of the plurality of tension lines is engaged with the frame. Each one of the plurality of retractor hooks are operable to engage with the flesh of a patient as each of the tension lines pull the flesh back laterally towards the frame along each side of the patient.

20 Claims, 15 Drawing Sheets

(56) References Cited

U.S. PATENT DOCUMENTS

2012/0136215 A1* 5/2012 Farley ................ A61B 17/0206
600/231

* cited by examiner

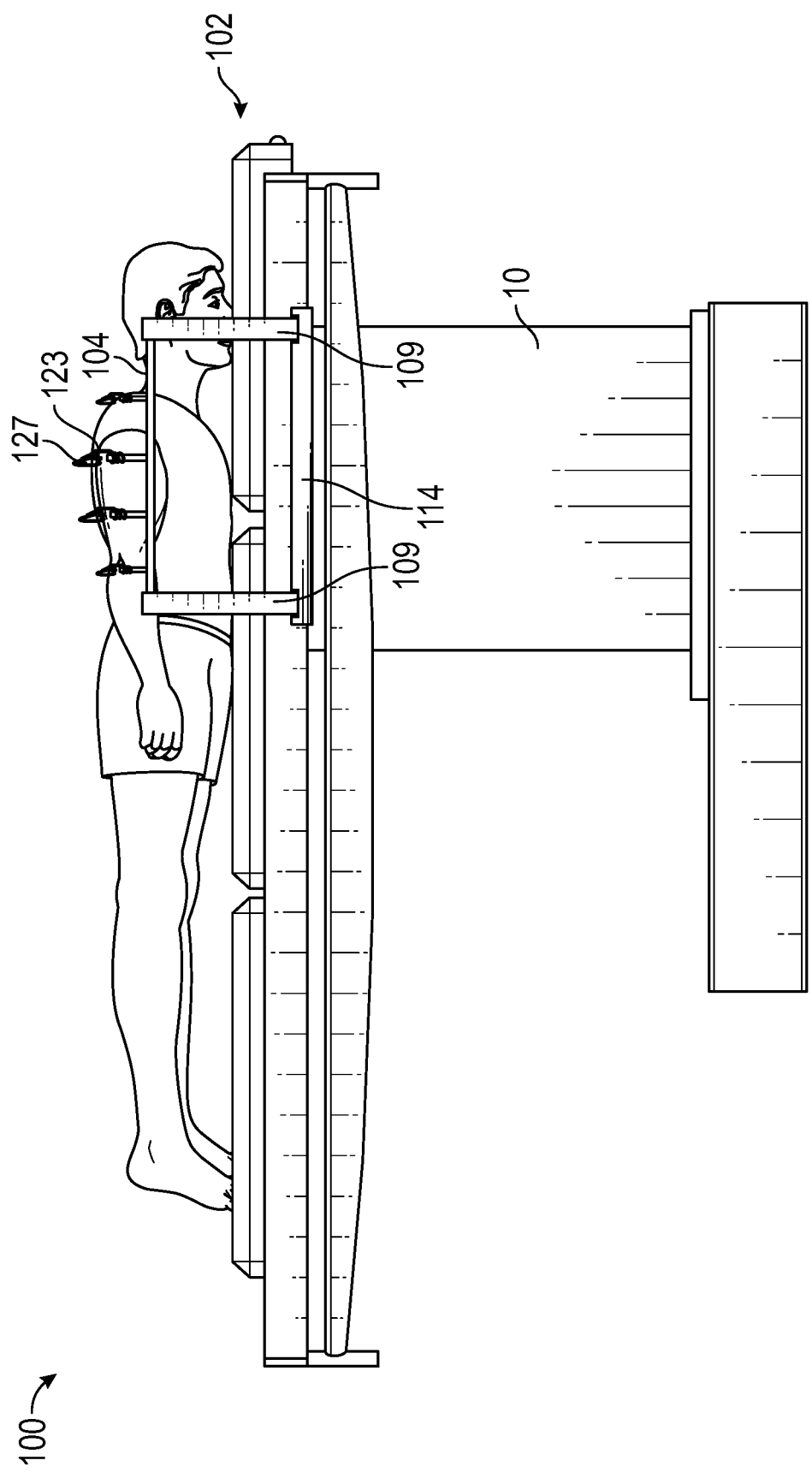

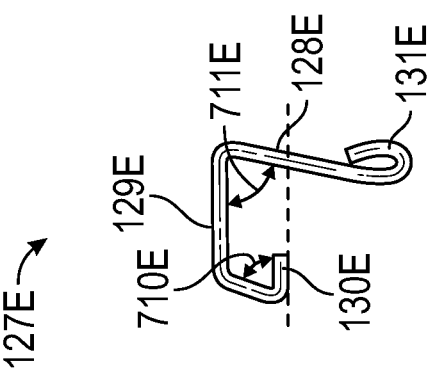
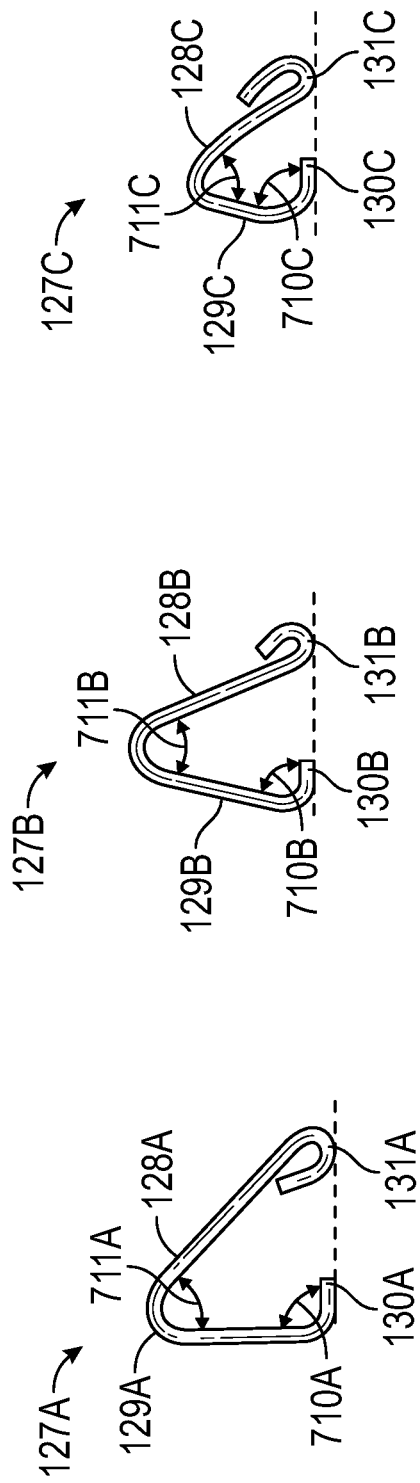
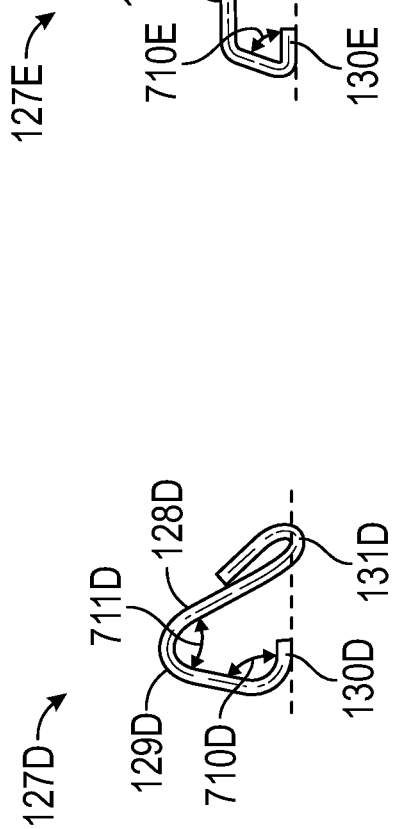

# TABLE MOUNTED RETRACTOR SYSTEM

CROSS REFERENCE TO RELATED APPLICATIONS

This is a PCT application that claims benefit from U.S. provisional application Ser. No. 62/656,422 filed on Apr. 12, 2018, which is incorporated by reference in its entirety.

FIELD

The present disclosure generally relates to surgical devices; and in particular, to systems and methods for a table-mounted retractor system that utilizes hooks, tension lines, and a table-mounted frame to retract tissue for open spine surgery.

BACKGROUND

For surgical operations, it is often necessary to use a retraction system to pull back skin, muscle, and other soft tissue in order to access internal organs, bones, and other structures in the body. For surgical operations which require access to large areas of the body, open-spine surgery for scoliosis correction in particular, a number of scissor-like self-retaining retractors are often positioned around the wound to hold the surrounding tissue in place. These retractors can sometimes be cumbersome to adjust or can cause accessibility issues, as well as may require more staff in the operating room to ensure a smooth operation. A versatile, easily adjusted and strong retractor system that allows full access to large areas of the body is desirable.

It is with these observations in mind, among others, that various aspects of the present disclosure were conceived and developed.

BRIEF DESCRIPTION OF THE DRAWINGS

FIGS. 1A and 1B are perspective views of one embodiment of a table-mounted tensioning retractor system, wherein FIG. 1A shows the table-mounted retractor system without a patient, and FIG. 1B shows the table-mounted retractor system with a patient.

FIG. 4 is a side view of the retractor system of FIG. 1.

FIG. 5 is an illustration showing multiple possible hook configurations with variations in hook length, shape and angle; showing each eyelet portion being lower than the hook portion.

FIGS. 6A and 6B are illustrations showing an embodiment of the retractor system using bungee cords as tensioners, wherein FIG. 6A is a view of a connection between the rod and the bungee cord tensioner, and FIG. 6B is a view of a connection between the bungee cord tensioner and a hook.

FIGS. 7A, 7B are illustrations showing an embodiment of the retractor system using wires as tensioners, wherein FIG. 7A is a view of a connection between the rod and the wire tensioner, and FIG. 7B is a view of a connection between the wire tensioner and a hook.

FIGS. 8A and 8B are illustrations showing an embodiment of the retractor system using springs as tensioners, wherein FIG. 8A is a view of a connection between the rod and the spring, and FIG. 8B is a view of a connection between the spring and a hook.

FIGS. 11A, 11B, 11C and 11D are illustrations showing multiple embodiments of the frame of the retractor system, wherein FIG. 11A shows the use of flip-locks to secure height, FIG. 11B shows the use of twist-locks to secure height, FIG. 11C shows the use of the bar disposed through one of a plurality of holes along the frame to secure height, and FIG. 11D shows the use of a spring-loaded button that may be pushed in or out of one of a plurality of holes disposed along the frame to secure height.

Corresponding reference characters indicate corresponding elements among the view of the drawings. The headings used in the figures do not limit the scope of the claims.

DETAILED DESCRIPTION

Figure 1A:
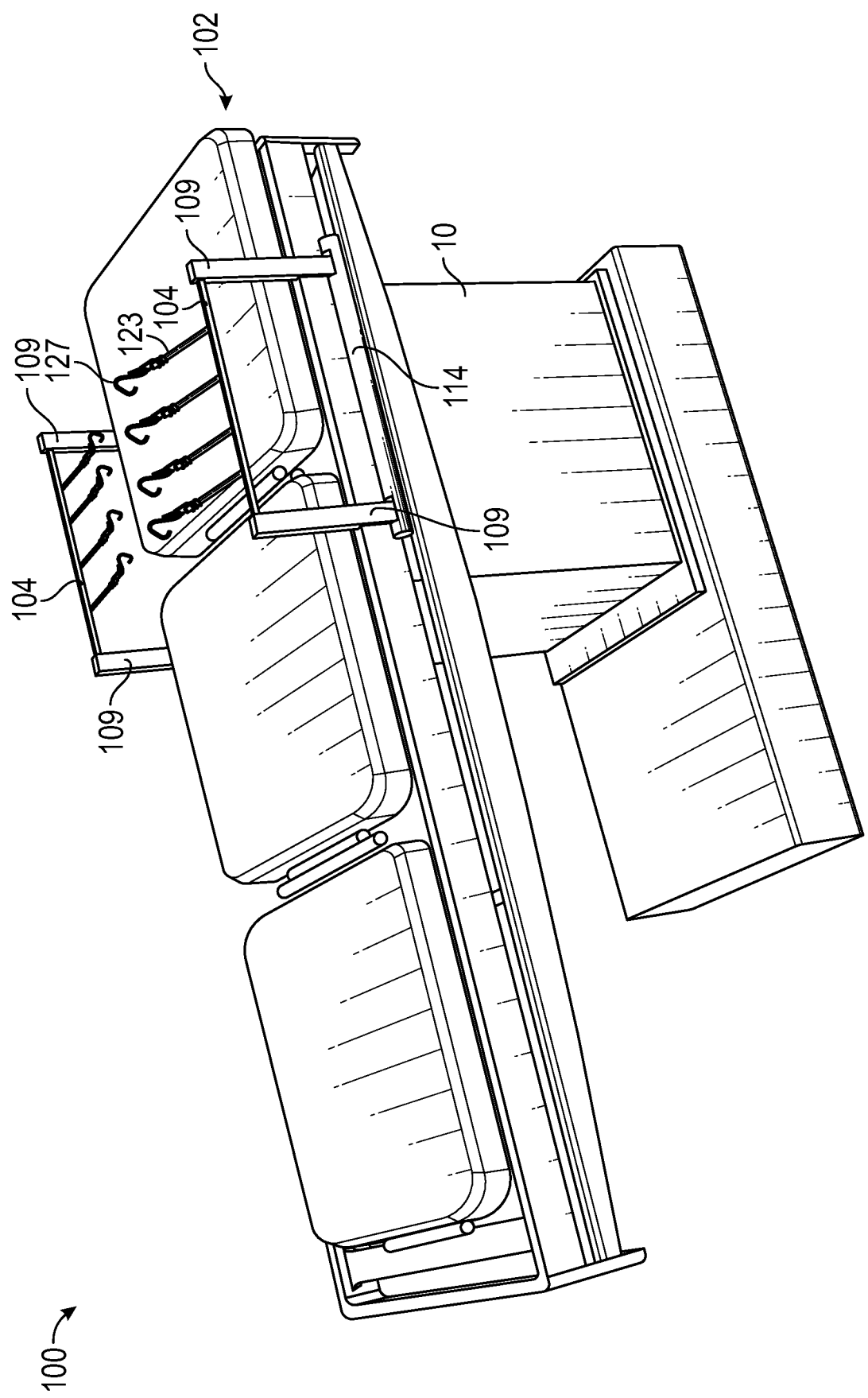
Figure 1B:
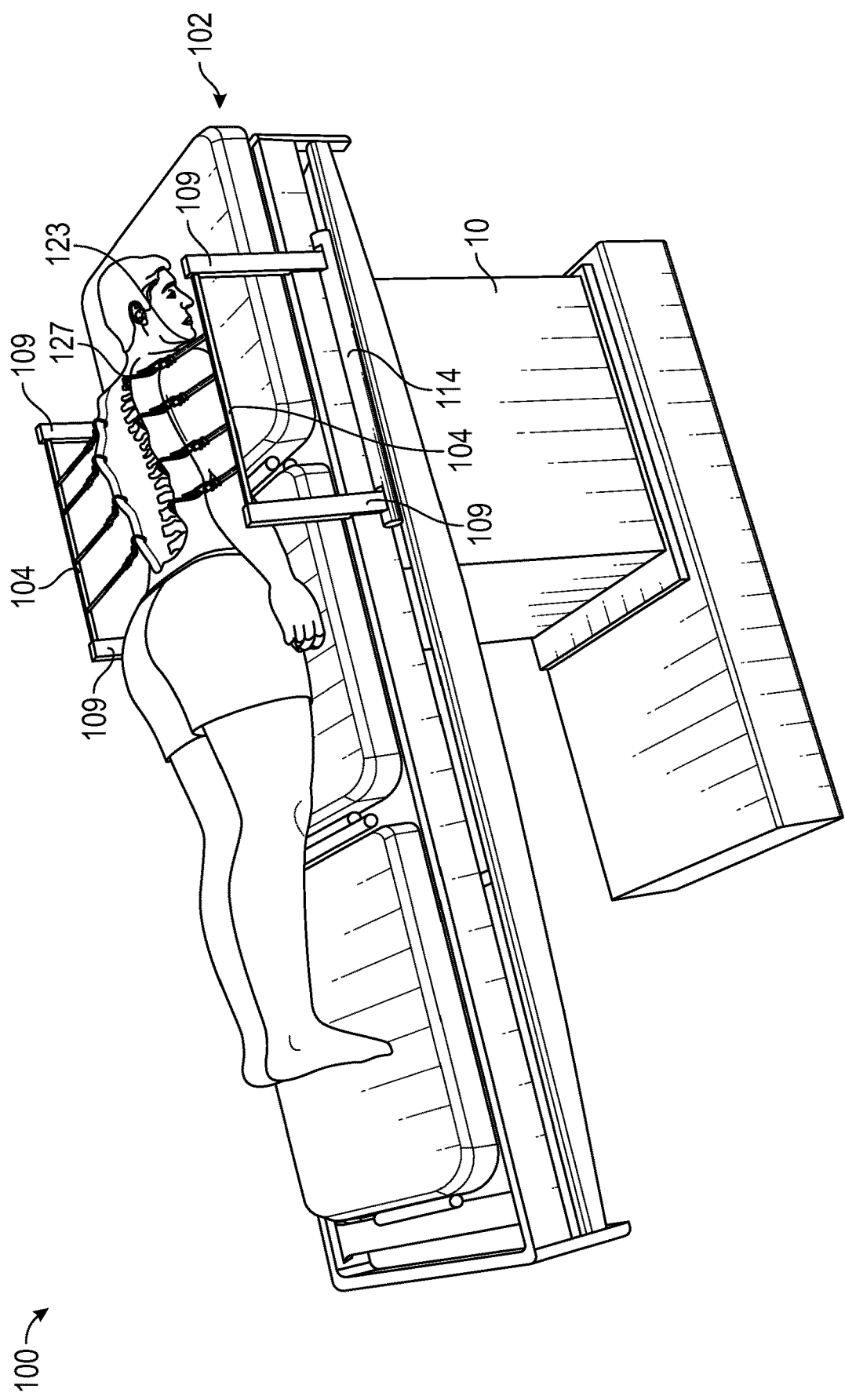
Figure 2:
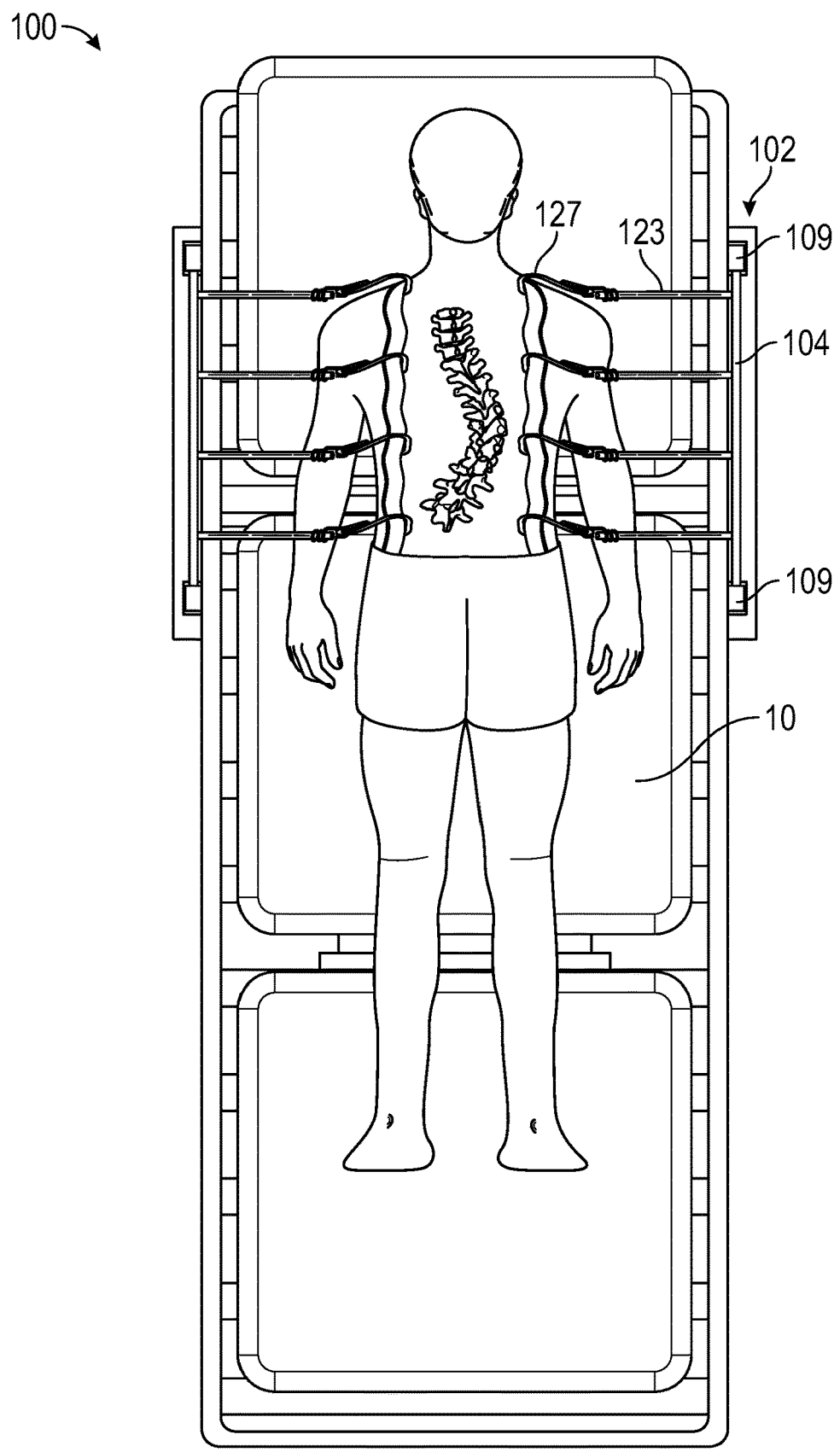
FIG. 2 is a top view of the retractor system of FIG. 1.
Figure 3:
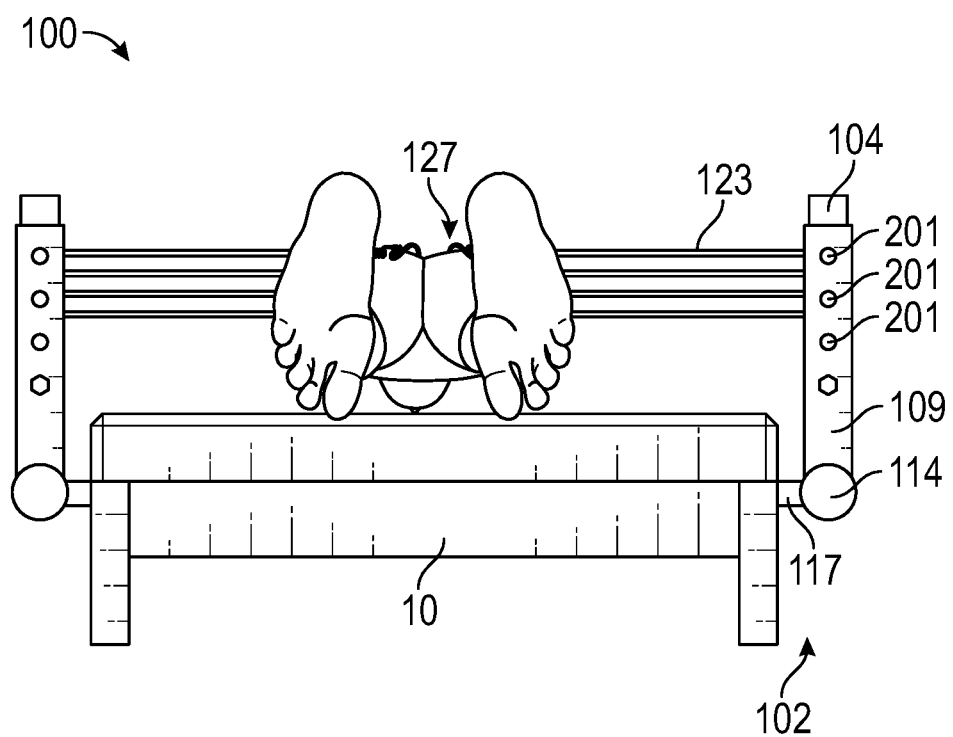
FIG. 3 is an end view of the retractor system of FIG. 1.

Various embodiments of a table-mounted retractor system for open-spine surgery are disclosed herein. In some embodiments, the table-mounted retractor system includes a frame, wherein the frame is situated lateral to the patient. In some embodiments, the table-mounted retractor system further comprises a plurality of retractor hooks wherein each of the plurality of retractor hooks are in operative association with one of a plurality of tension lines, wherein each of the plurality of tension lines is engaged with the frame. In one method, each one of the plurality of retractor hooks are operable to engage with the flesh of a patient as each of the tension lines pull the flesh back laterally towards the frame along each side of the patient.

In some embodiments, the frame is operable for variable height, variable frame width, and variable frame angle of the table mounted retractor system and comprises a pair of longitudinal rods, wherein each of the pair of longitudinal rods is supported by a plurality of vertical rods and each of the pair of longitudinal rods are operable for varying the length of each of the pair of longitudinal rods. Each of the plurality of vertical rods is configured to be affixed to an operating table and may be angled towards or away from the patient. Referring to the drawings, embodiments of a table-mounted retractor system are illustrated and generally indicated as 100 in FIGS. 1-14.

Referring to FIGS. 1-4, in some embodiments the table-mounted retractor system 100 may include a frame 102 comprising a pair of longitudinal rods 104 coupled to a plurality of vertical rods 109 (each defining an upper portion 109A and a lower portion 109B), wherein each of the pair of longitudinal rods 104 are situated parallel to the sides of an operating table 10 and are supported by the upper portion 109A of each of the plurality of vertical rods 109. In some embodiments, a plurality of lateral rods 117 may connect the lower portion 109B of each one of the plurality of vertical rods 109 at the sides of an operating table 10, wherein a junction between each one of the plurality of vertical rods 109 and each of the lateral rods 117 defines a pivoting joint 114. The table-mounted retractor system 100 further comprises a plurality of tension lines 123, each defining a distal portion 123A and a proximal portion 123B, and a plurality of retractor hooks 127, wherein each of the plurality of retractor hooks 127 comprises a hook arm 129 and an eyelet loop 131. Each distal portion 123A of the plurality of tension lines 123 is affixed to each one of the pair of longitudinal rods 104, and each proximal portion 123B of each of the plurality of tension lines 123 are configured to engage with the eyelet loop 131 of each one of the plurality of retractor hooks 127.

Five separate embodiments of the retractor hook (designated 127A-127E) are shown in FIGS. 5A, 5B, 5C, 5D and 5E, respectively. The general description of the retractor hook 127 will be discussed by way of example using retractor hook 127A in which this description will apply to the other retractor hooks 127B-127E.

In operation, the barb 130A of the retractor hook 127A engages with the flesh of the patient after an incision has been made and the hook arm 129A retracts the flesh laterally, thereby allowing access to the spine or other structures in the body. The eyelet loop 131A of each of the plurality of retractor hooks 127A engages with a respective tension line 123, wherein the tension line 123 applies a force that pulls the retractor hook 127A laterally towards the longitudinal rod 104, thereby retracting the flesh of the patient by the retractor hook 127A. The barb 130A of the retractor hook 127A curves inward and a barb angle 710A defined between the barb 130A and the lower portion of the hook arm 129A may vary depending on the surgeon's preference. The barb angle 710A may also vary in sharpness. The eyelet loop 128A of the retractor hook 127 may curve either inward or outward and vary in length. During operation, the eyelet loop 131A of the retractor hook 127A must always be situated at the same depth or deeper than the barb 130A relative to the patient to prevent the retractor hook 127A from being unintentionally being disengaged or otherwise pulled out of the patient. When tension is applied to the eyelet 131A, the barb 130A either does not rotate (if the eyelet 131A and barb 130A are at the same depth relative to the top of the incision) or the barb rotates further into the patient (if the eyelet 131A is deeper than the barb 130A) thereby, further securing the barb 130A into the patient's tissue. If the eyelet 131A is not as deep as the barb 130A relative to the relative to the top of the incision, then when tension is applied at the eyelet 131A, the barb 130A will rotate out of the patient and stop functioning as a retractor, which would be undesirable.

Referring to FIG. 5A, the hook arm 129A of the retractor hook comprises an upper portion and a lower portion, wherein a barb 130A protrudes from the lower portion of the hook arm 129A. In operation, the barb 130A engages with the flesh of the individual to prevent the retractor hook 127A from slipping out of place, as shown in the configuration of the retractor hook 127 in FIG. 14. In FIG. 5A, the retractor hook 127A further comprises an eyelet arm 128A having an upper portion and a lower portion, wherein the eyelet loop 131A protrudes from the lower portion of the eyelet arm 128A. A junction of the upper portion of the hook arm 129A and the upper portion of the eyelet arm 128A create a hook angle 711A. FIG. 5A shows the eyelet 131A looping in a medial direction (inward) with the barb angle 710A being a 90 degree angle. In addition, when a line following the barb 130A is visualized as shown in FIG. 5A, the eyelet loop 131A is shown at the same level as the barb 130A, thus ensuring that the condition for a stable retraction is met.

FIG. 5B similarly shows a separate embodiment of the retractor hook 127B, wherein the hook arm 129B similarly comprises an upper portion and a lower portion, wherein a barb 130B protrudes from the lower portion of the hook arms 129B. In operation, the barb 130B engages with the flesh of the individual. In FIG. 5B, the retractor hook 127B further comprises an eyelet arm 128B having an upper portion and a lower portion, wherein the eyelet loop 131B protrudes from the lower portion of the eyelet arm 128B. A junction of the upper portion of the hook arm 129B and the upper portion of the eyelet arm 128B create a hook angle 711B. In the case of the embodiment shown in FIG. 5B, the eyelet loop 131B loops in a lateral direction (outward) and the barb angle 710B is less than 90 degrees. Similarly to the embodiment of FIG. 5A, when a line following the barb 130B is visualized as shown in FIG. 5B, the eyelet loop 131B is shown at the same level as the barb 130B.

FIG. 5C similarly shows a separate embodiment of the retractor hook 127C, wherein the hook arm 129C similarly comprises an upper portion and a lower portion, wherein the barb 130C engages with the flesh of the individual. In FIG. 5C, the retractor hook 127C further comprises an eyelet arm 128C having an upper portion and a lower portion, wherein the eyelet loop 131C protrudes from the lower portion of the eyelet arm 128C. A junction of the upper portion of the hook arm 129C and the upper portion of the eyelet arm 128C create a hook angle 711C. In the case of the embodiment shown in FIG. 5C, the eyelet loop 131C is elongated in comparison with the eyelet loops 131A and 131B of FIGS. 5A and 5B. In addition, the barb angle 710C is softened. The eyelet arm 128C is shown having a very slight curve to it. Similarly to the embodiment of FIGS. 5A and 5B, when a line following the barb 130C is visualized as shown in FIG. 5C, the eyelet loop 131C is shown at the same level as the barb 130C.

FIG. 5D shows an embodiment of a retractor hook 127D that has structural similarities to the embodiment of FIG. 5C, however the eyelet arm 131D of the embodiment of FIG. 5D is shown to be considerably longer than the eyelet arm 131C. Thus, when a line following the barb is visualized as shown in FIG. 5D, the eyelet loop 131D is shown to be below the barb 130D, thus ensuring that the condition for a stable retraction is met.

FIG. 5E shows another valid embodiment of the retractor hook 127, herein referred to as 127E. In this embodiment, the hook arm 129E comprises an additional turn before the barb angle 710E. In this manner, when the line following a barb 130E visualized in FIG. 5E, the eyelet loop 131E is shown to be far below the line, thus satisfying the condition to ensure that the retractor hook 127E functions properly.

Furthermore, as shown in FIGS. 5A, 5B, 5C, 5D and 5E, the hook angle 711A-711E of each retractor hook 127A-127E may also vary in sharpness. In other embodiments (not shown), a single retractor hook 127 may comprise multiple hook arms (not shown) and one eyelet arm (not shown) to retract a wider portion of the patient's flesh. The sizes and shapes of each of the plurality of retractor hooks 127 may vary in order to allow for a customizable system that a surgeon may use at their discretion.

Figure 6A:
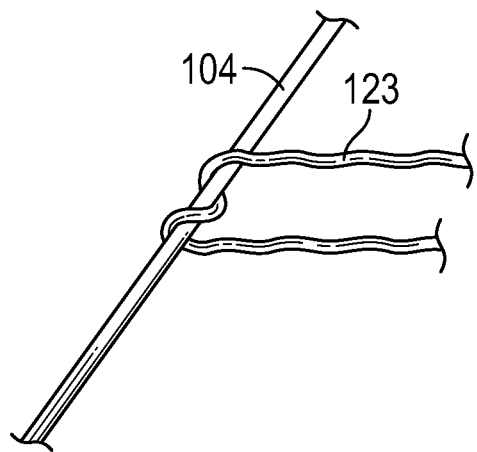
Figure 6B:
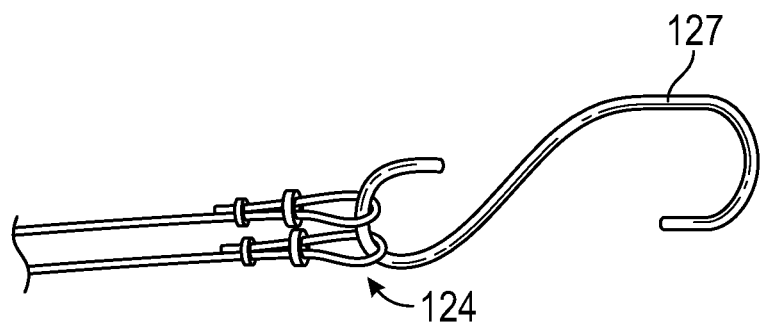
Figure 11A:
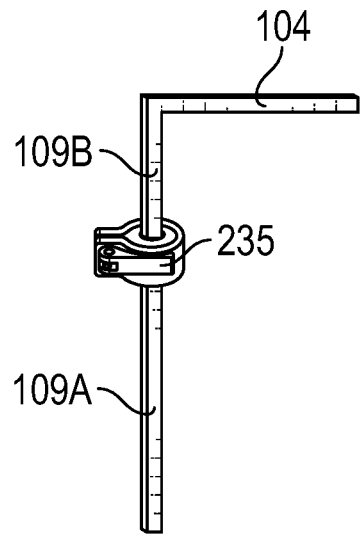
Figure 11B:
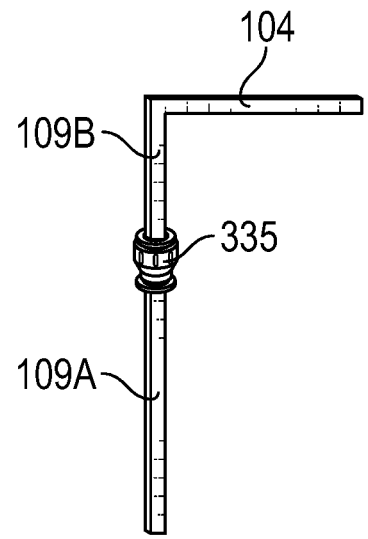

In some embodiments, each of the plurality of tension lines 123 defines a distal portion 123A and a proximal portion 123B. In addition, each of the plurality of tension lines 123 connects each one of the plurality of retractor hooks 127 with each one of the pair of longitudinal rods 104. Each eyelet loop 131 of a respective retractor hook 127 is connected with the proximal portion 123B of a respective one of the plurality of tension lines 123, and each distal portion 123A of each of the plurality of tension lines 123 is connected with one of each of the pair of longitudinal rods 104. Referring to FIGS. 6A and 6B, in some embodiments, the tension lines 123 may be comprised of an elastic cord (such as bungee cord or rubber band) having small hooks 124 on each end, wherein the middle of the elastic cord is wrapped around the longitudinal rod 104 several times, as shown in FIG. 6, and doubled up such that both hooks 124 may be secured with the eyelet loop 131 of the retractor hook 127, as shown in FIG. 11B. Alternatively, the tension line is a loop (not shown) that is secured to the eyelet 131 and wrapped around the longitudinal rod 104 any number of times to obtain the desired tension on the retractor hook 127.

Figure 7A:
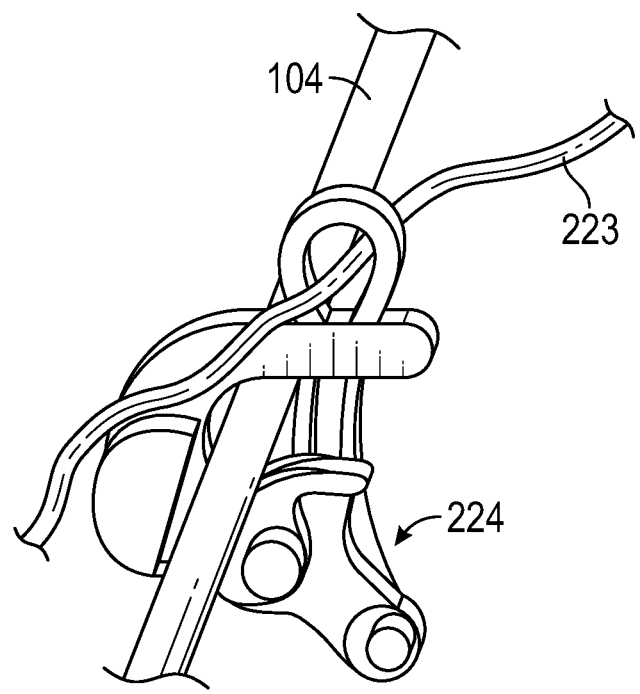
Figure 7B:
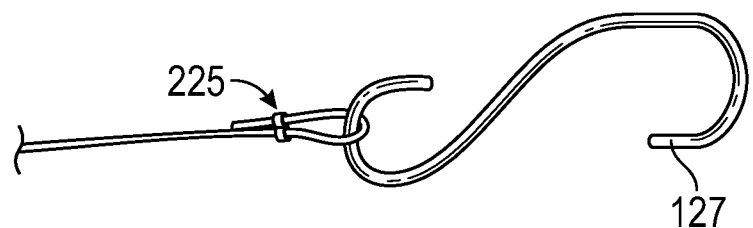

Referring to FIGS. 7A and 7B, in other embodiments, the tension on each retractor hook 127 may be provided by a wire tension line 223 defining a distal portion 223A and a proximal portion 223B. The distal portion 223A of each wire tension line 223 may be secured to each of the pair of longitudinal rods 104 using a wire grip 224, such that the wire tension line 223 may be tightened appropriately, as shown in FIG. 7A. Each wire tension line 223 may be secured to each of the plurality of retractor hooks 127 by looping the proximal portion 223B of each wire tension line 223 through the eyelet loop 131 of the respective retractor hook 127 and crimping the end of the proximal portion 223B of the wire tension line 223 to the beginning of the eyelet loop 131, as shown in FIG. 7B.

Figure 8A:
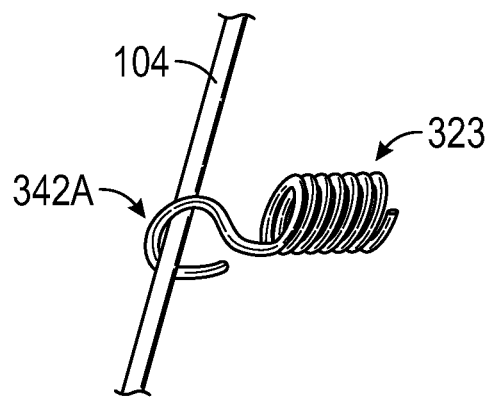
Figure 8B:
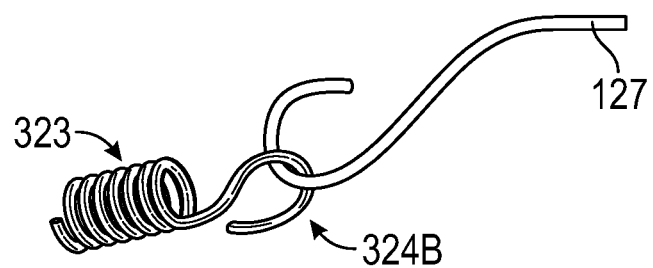
Figure 9:
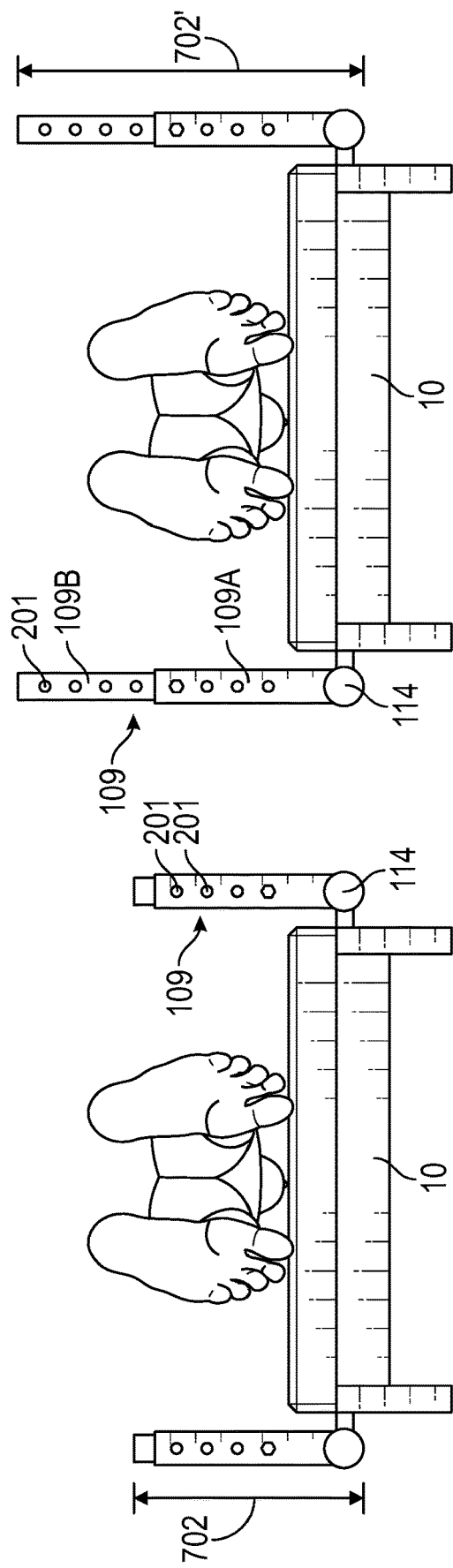
FIG. 9 is an illustration demonstrating the variable height of the frame of the retractor system of FIG. 1.

Referring to FIGS. 8A and 8B, in other embodiments, the wire or elastic tensioning method may be traded for a spring tension line 323 having a distal hook 324A and a proximal hook 324B, wherein the distal hook 324A of each of the plurality of spring tension lines 323 may be hooked onto each of the pair of longitudinal rods 104 as shown in FIG. 8A. Similarly, the proximal hooks 324B may be disposed through the eyelet loop 131 of each respective retractor hook 127, as shown in FIG. 8B.

Other embodiments that are not pictured may use link chains, beaded pull chains, rods, or even string to provide tension between the plurality of retractor hooks 127 and each of the longitudinal rods 104.

In some embodiments, each one of the plurality of vertical rods 109 is configured for variable height. In one embodiment shown in FIG. 9, each one of the plurality of vertical rods 109 is divided into a large telescoping section 109A and a small telescoping section 109B, wherein the small telescoping section 109B is disposed within the large telescoping section 109A and the small telescoping section 109B may be lifted or lowered relative to the large telescoping section 109A to create a variable frame height 702. The small telescoping section 109B and the large telescoping section 109A are joined and held in their respective positions using a vertical lock 112, as shown in FIGS. 11A and 11B wherein FIG. 11A shows the use of a flip lock 235 and FIG. 11B shows the use of a twist lock 335.

Figure 12:
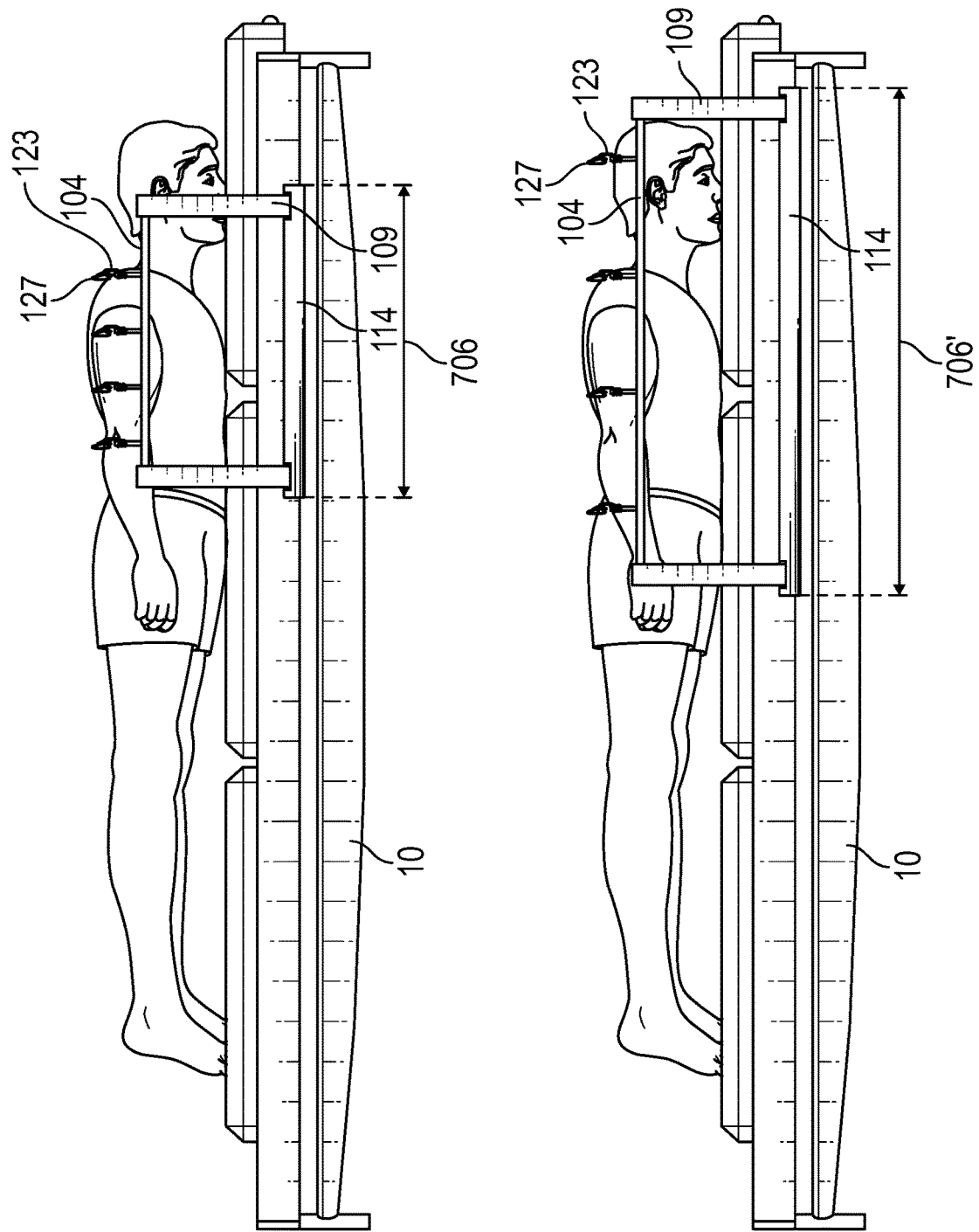
FIG. 12 is an illustration showing the variable length of the frame of the retractor system of FIG. 1.

Similar to the telescoping configuration of the vertical rods 109, each of the pair of longitudinal rods 104 is similarly configured for variable length, as shown in one embodiment in FIG. 12. Similar to the plurality of vertical rods 109, each of the pair of longitudinal rods 104 may be divided into a large telescoping section 104A and a small telescoping section 104B, wherein the small telescoping section 104B is similarly disposed within the large telescoping section 104A and the small telescoping section 104B and the large telescoping section 104A are joined and held in place by a longitudinal lock 107. By moving the small telescoping section 104B relative to the large telescoping section 104A, a variable frame length 706 may be established.

Figure 13:
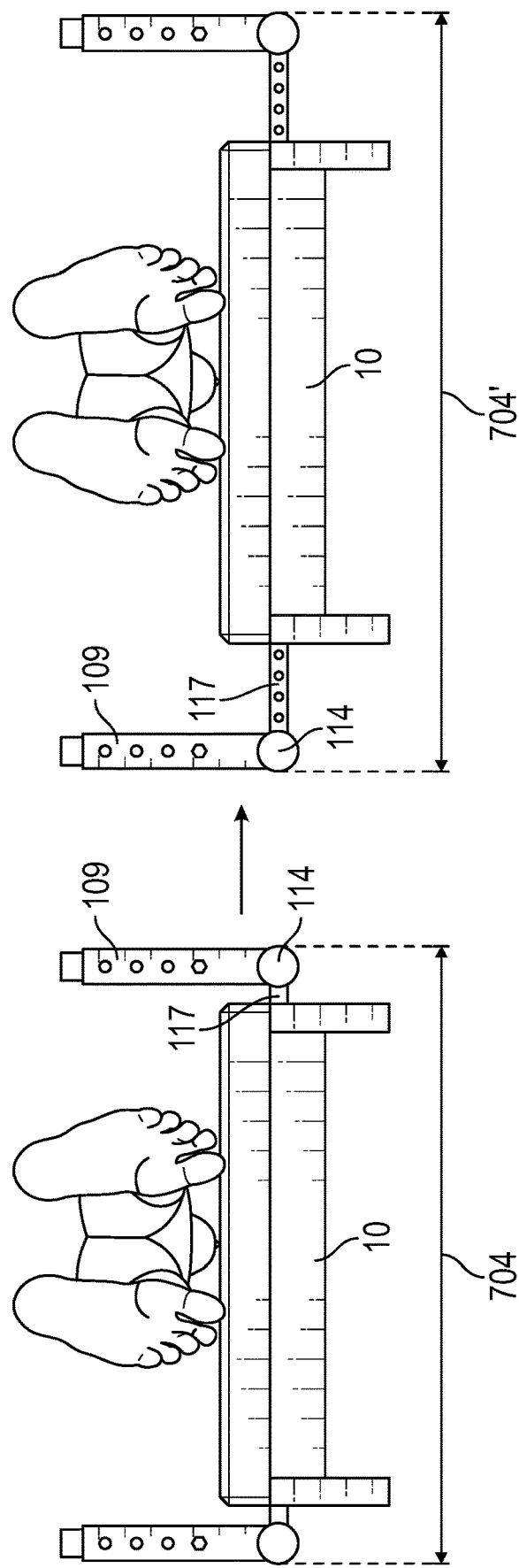
FIG. 13 is an illustration showing the variable width of the frame of the retractor system of FIG. 1.
Figure 14:
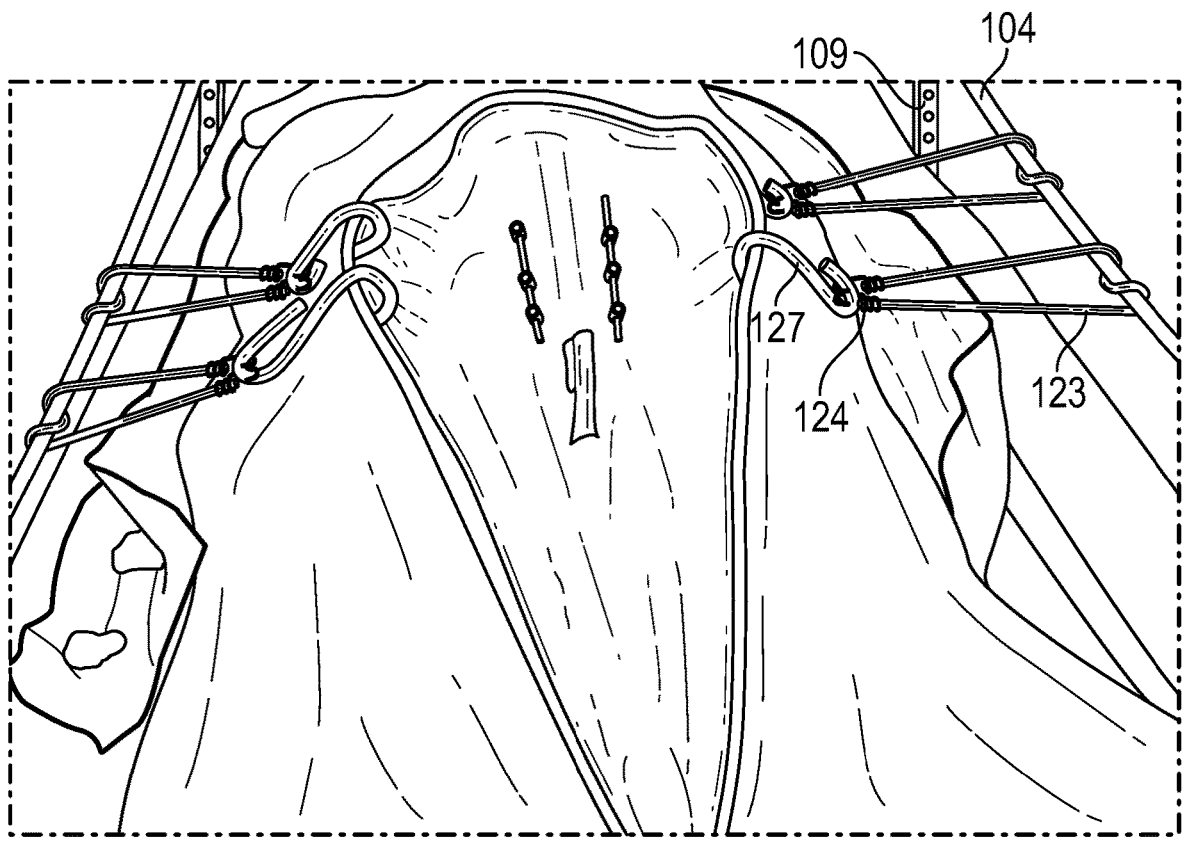
FIG. 14 is an illustration showing the retraction hooks and tension lines in operation, holding back soft tissue.

Referring to FIG. 13, each one of the plurality of vertical rods 109 may be attached to the bed through a lateral rod 117 which extends laterally from the large telescoping section 110 towards the operating table 10. Each of the plurality of lateral rods 117 may be attached to the underside 11 of the operating table 10 using screws or clamps (not shown).

Much like each of the plurality of vertical rods 109 and each one of the pair of longitudinal rods 104, each one of the plurality of lateral rods 117 may also have a telescoping configuration, wherein the lateral rod 117 comprises a large telescoping section 117A and a small telescoping section 117B, wherein the small telescoping section 117B is disposed through the large telescoping section 117A, creating a variable frame width 704. The large telescoping section 117A and the small telescoping section 117B are also joined with a lateral lock 120.

Figure 10:
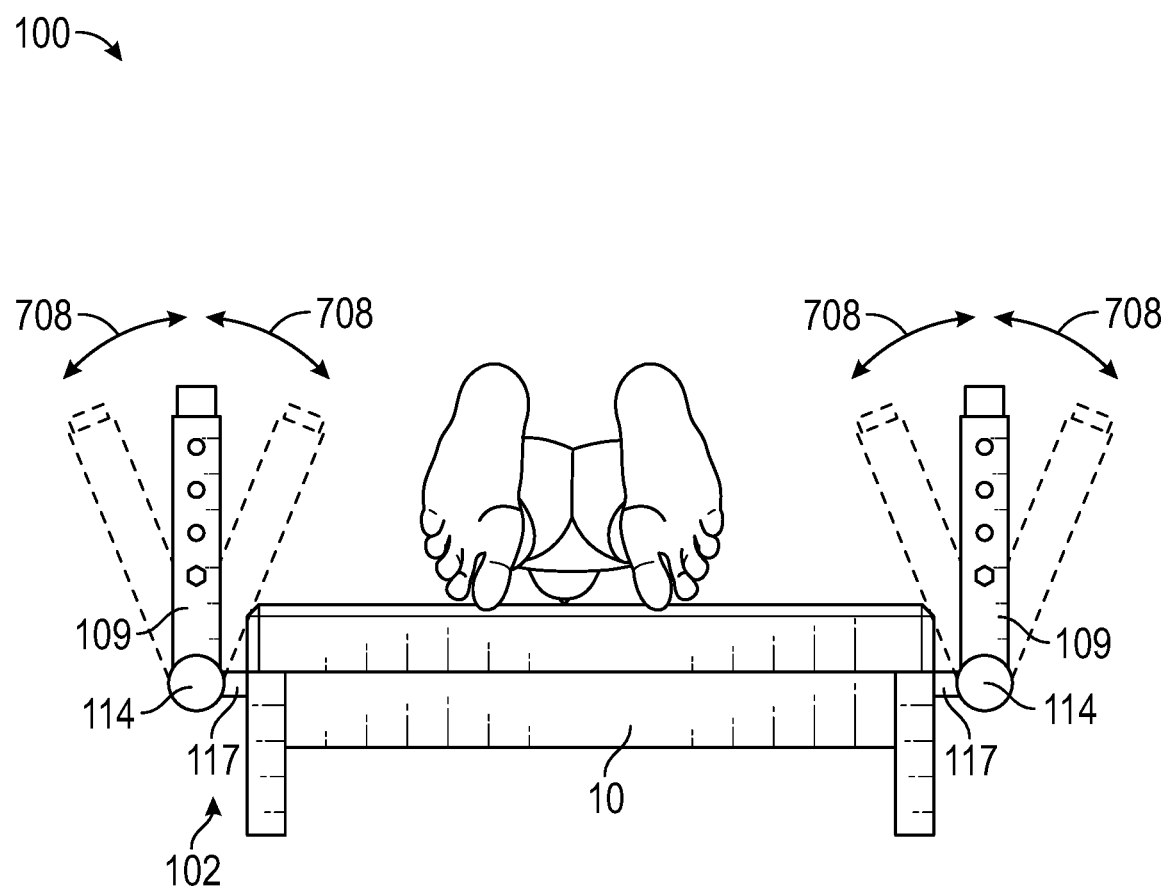
FIG. 10 is an illustration demonstrating the pivotal movement of the frame of the retractor system of FIG. 1.

As shown in FIG. 10, each one of the plurality of vertical rods 109 are connected with each one of the plurality of lateral rods 117 using a respective pivoting joint 114, creating a variable frame angle 708 defined between each one of the plurality of vertical rods 109 and each one of the plurality of lateral rods 117, as shown in FIG. 10. The frame angle 708 may vary relative to the perpendicular. In some embodiments, each one of the plurality of pivoting joints 114 may have a pivoting joint lock 115 to prevent unintentional change of the frame angle 708. In some embodiments, one large pivoting joint 114 is situated at a junction between each of the plurality of vertical rods 109 and a frame of the surgical table 10 (as shown in FIG. 10). The one or more pivoting joints 114 may be placed at any point along each of the plurality of vertical bars 109. In other embodiments, a plurality of pivoting joints 114 are included at each junction between each of the plurality of vertical rods 109 and the frame of a surgical table 10 to allow for custom stabilizing frame shapes to accommodate variable patient sizes and shapes.

Figure 11C:
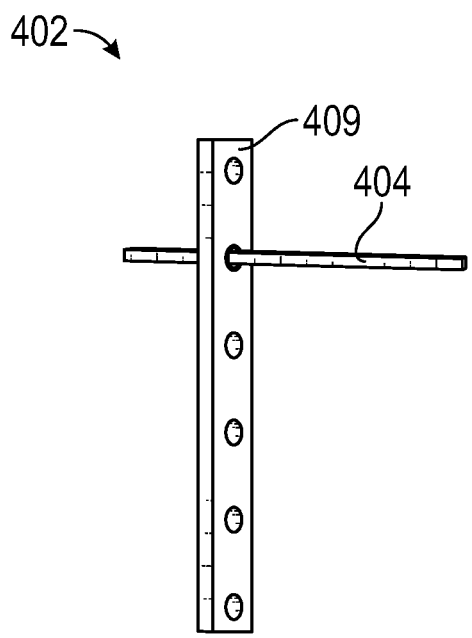

Other embodiments may modulate the frame height 702 by forgoing a telescoping configuration and introducing an alternative frame 402, shown in FIG. 11C, wherein each one of the plurality of vertical rods 109 is replaced with an alternative vertical rod 409 comprising a plurality of holes 410 disposed along the alternative vertical rod 409. A pair of alternative longitudinal rods 404 having a proximal portion 404A and a distal portion (not shown), wherein the alternative longitudinal rod 404 is smaller in diameter than each of the plurality of holes 410. The alternative longitudinal rod 404 may be disposed through one of the plurality of holes 410 defined along each one of the plurality of alternative vertical rods 409. By choosing a superior one of the plurality of holes 401 the variable frame height 702 may be increased, and by choosing an inferior one of the plurality of holes 401 the variable frame height 702 may be decreased.

Figure 11D:
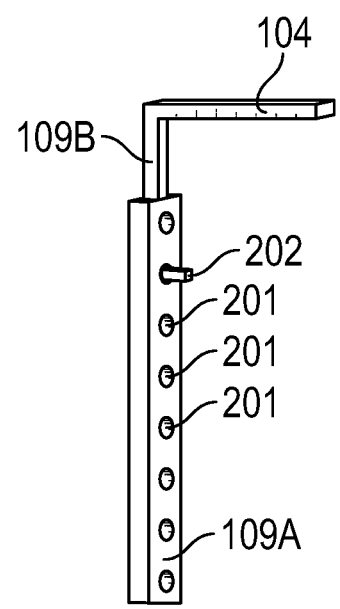

Other embodiments may alter the telescoping configuration of each one of the plurality of vertical rods 109 by adding a plurality of holes 201 along the large telescoping section 109A of the vertical rod 109 and by adding a spring-loaded button 202 to the small telescoping section 109B of the vertical rod 109 such that variable frame height 702 may be achieved by pushing the spring-loaded button 202 and pulling or pushing the small telescoping section 109 such that the spring-loaded button 202 may be disposed through one of the plurality of holes 201, as shown in FIG. 11D. By choosing a superior one of the plurality of holes 201 the variable frame height 702 may be increased, and by choosing an inferior one of the plurality of holes 201 the variable frame height 702 may be decreased. Similarly, a spring-loaded button (not shown) may be added to the small telescoping section 104B of the longitudinal rod 104 and a plurality of holes (not shown) may be added to the large telescoping section 104A of the longitudinal rod 104 such that the variable frame length 706 may be modulated in a similar manner to that of the variable frame height 702. In addition, a spring-loaded button (not shown) may also be added to the small telescoping section 117B of the lateral rod 117 and a plurality of holes (not shown) may be added to the large telescoping section 117A of the lateral rod 117 such that the variable frame width 704 may be modulated in a similar manner to that of the variable frame height 702 and the variable frame length 706 described above.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A surgical retractor system, comprising:
    a table-mounted frame, comprising:
        a pair of longitudinal rods, and
        a plurality of vertical rods, each defining an upper portion and a lower portion;
        wherein each of the pair of longitudinal rods are perpendicularly coupled to the upper portion of the plurality of the vertical rods;
    a plurality of surgical retractor hooks operatively connected to the table-mounted frame,
        wherein each of the plurality of surgical retractor hooks defines:
            an eyelet arm defining an eyelet loop formed at one end portion of the eyelet arm, the eyelet loop having a bent configuration that forms an opening; and
            a hook arm forming a barb at an opposite end portion of the hook arm;
        wherein the barb of each of the plurality of surgical retractor hooks is operable to engage with the flesh of a patient and the eyelet loop of each of the plurality of surgical retractor hooks is operable to be positioned lateral to the patient; and
    a plurality of tension lines operatively engaged between the table-mounted frame and a respective one of the plurality of surgical retractor hooks;
        wherein each of the plurality of tension lines define:
            a distal end; and
            a proximal end;
            wherein the proximal end of each of the plurality of tension lines are operable to engage with the table-mounted frame and the distal end of each of the plurality of tension lines are operable to engage with the eyelet loop of one of a plurality of surgical retractor hooks;
            wherein each of the plurality of tension lines apply a force that pulls each respective one of the plurality of surgical retractor hooks in a lateral direction.

2. The surgical retractor system of claim 1, wherein each of the plurality of vertical rods defines a plurality of holes, wherein each of the pair of longitudinal rods is disposed through one of the plurality of holes of each one of the vertical rods.

3. The surgical retractor system of claim 1, wherein each of the plurality of vertical rods comprises a large telescoping section and a small telescoping section, wherein the small telescoping section is disposed within the large telescoping section, wherein the small telescoping section and the large telescoping section are joined and operable to be held in place with a fastener.

4. The surgical retractor system of claim 3, wherein the small telescoping section is operable to be lifted or lowered relative to the large telescoping section.

5. The surgical retractor system of claim 1, wherein each of the pair of longitudinal rods comprises a large telescoping section and a small telescoping section, wherein the small telescoping section is disposed within the large telescoping section, wherein the small telescoping section and the large telescoping section are joined and operable to be held in place with a fastener.

6. The surgical retractor system of claim 5, wherein the small telescoping section is operable to be moved in an axial direction or an opposite axial direction relative to the large telescoping section.

7. The surgical retractor system of claim 1, further comprising:
    a plurality of lateral rods; and
    a plurality of pivotable joints;
    wherein each of the plurality of vertical rods are operatively engaged with a respective one of a plurality of lateral rods using a pivotable joint;
    wherein a junction between each of the plurality of vertical rods and each respective one of the plurality of lateral rods defines a pivot angle;
    wherein each of the plurality of lateral rods are operable to directly affix to a surgical table.

8. The surgical retractor system of claim 7, wherein the pivot angle is operable to be adjusted.

9. The surgical retractor system of claim 7, wherein the pivot joint is operable to be held in place with a fastener.

10. The surgical retractor system of claim 7, wherein each of the plurality of lateral rods comprises a large telescoping section and a small telescoping section, wherein the small telescoping section is disposed within the large telescoping section, wherein the small telescoping section and the large telescoping section are joined and operable to be held in place with a fastener.

11. A surgical retractor system, comprising:
    a table-mounted frame, comprising:
        a pair of longitudinal rods, and
        a plurality of vertical rods, each defining an upper portion and a lower portion;
        wherein each of the pair of longitudinal rods are perpendicularly coupled to the upper portion of the plurality of the vertical rods;
    a plurality of surgical retractor hooks operatively connected to the table-mounted frame,
        wherein each of the plurality of surgical retractor hooks defines:
            an eyelet arm defining an eyelet loop; and
            a hook arm forming a barb at an opposite end portion of the hook arm;
        wherein the barb of each of the plurality of surgical retractor hooks is operable to engage with the flesh of a patient and the eyelet loop of each of the plurality of surgical retractor hooks is operable to be positioned lateral to the patient; and
    a plurality of tension lines operatively engaged between the table-mounted frame and a respective one of the plurality of surgical retractor hooks;
        wherein each of the plurality of tension lines define:
            a distal end; and
            a proximal end;
            wherein the proximal end of each of the plurality of tension lines are operable to engage with the table-mounted frame and the distal end of each of the plurality of tension lines are operable to engage with the eyelet loop of one of a plurality of surgical retractor hooks;

wherein each of the plurality of tension lines apply a force that pulls each respective one of the plurality of surgical retractor hooks in a lateral direction;
wherein each of the plurality of tension lines apply a force that pulls each respective one of the plurality of surgical retractor hooks in a lateral direction wherein each of the plurality of tension lines comprises an elastic cord; wherein the elastic cord defines a proximal hook and a distal hook; wherein the distal portion of the tension line is engaged to the frame by looping the middle of the elastic cord around the frame and the proximal portion of the tension line is engaged to the eyelet loop of one of a plurality of surgical retractor hooks using the distal hook and the proximal hook.

12. The surgical retractor system of claim 1, wherein each of the plurality of tension lines comprises wire; wherein the proximal portion of the tension line is engaged to the frame using a wire grip and wherein the distal portion of the tension line is engaged to the eyelet loop of one of a plurality of surgical retractor hooks by looping the distal portion of the tension line around the eyelet loop.

13. A surgical retractor system, comprising:
a table-mounted frame, comprising:
a pair of longitudinal rods, and
a plurality of vertical rods, each defining an upper portion and a lower portion;
wherein each of the pair of longitudinal rods are perpendicularly coupled to the upper portion of the plurality of the vertical rods;
a plurality of surgical retractor hooks operatively connected to the table-mounted frame,
wherein each of the plurality of surgical retractor hooks defines:
an eyelet arm defining an eyelet loop; and
a hook arm forming a barb at an opposite end portion of the hook arm;
wherein the barb of each of the plurality of surgical retractor hooks is operable to engage with the flesh of a patient and the eyelet loop of each of the plurality of surgical retractor hooks is operable to be positioned lateral to the patient; and
a plurality of tension lines operatively engaged between the table-mounted frame and a respective one of the plurality of surgical retractor hooks;
wherein each of the plurality of tension lines define:
a distal end; and
a proximal end;
wherein the proximal end of each of the plurality of tension lines are operable to engage with the table-mounted frame and the distal end of each of the plurality of tension lines are operable to engage with the eyelet loop of one of a plurality of surgical retractor hooks;
wherein each of the plurality of tension lines apply a force that pulls each respective one of the plurality of surgical retractor hooks in a lateral direction
wherein each of the plurality of tension lines comprises a spring, wherein the spring defines a proximal hook and a distal hook; wherein the distal portion of the tension line is engaged to the frame using the proximal hook and the proximal portion of the tension line is engaged to the eyelet loop of one of a plurality of surgical retractor hooks using the distal hook.

14. A surgical retractor hook, comprising:
a hook arm, comprising a barb; and
an eyelet arm, comprising an eyelet loop having an opening formed by the bent configuration of the eyelet arm;
wherein a junction of the hook arm and the eyelet arm define a hook angle;
wherein a junction of the hook arm and the barb define a barb angle;
wherein during operation the surgical retractor hook is rotated such that the eyelet loop is lower than the barb;
wherein the barb is operable to engage with the flesh of a patient and the eyelet loop is operable to engage with one of a plurality of tension lines.

15. The surgical retractor hook of claim 14, wherein the surgical retractor hook comprises a plurality of hook arms.

16. The surgical retractor hook of claim 14, wherein the barb curves in a medial direction.

17. The surgical retractor hook of claim 14, wherein the eyelet loop curves in a medial direction.

18. The surgical retractor hook of claim 14, wherein the eyelet loop curves in a lateral direction.

19. A method for retracting tissue using a table-mounted retractor system, comprising:
inserting a plurality of surgical retractor hooks into the flesh of a patient such that a hook arm of each of the plurality of surgical retractor hooks engages directly with the flesh and an eyelet arm of each of the plurality of surgical retractor hooks defines an eyelet loop having an opening formed by the bent configuration of the eyelet arm for each of the surgical retractor hooks is situated posterior to the hook arm; and
applying force to each of the plurality of surgical retractor hooks in a lateral direction and such that the eyelet loop is pulled in a similar lateral direction, wherein the force is applied to each of the plurality of surgical retractor hooks by a plurality of tension lines;
wherein the application of force in a lateral direction to each of the plurality of surgical retractor hooks thereby applies a lateral force to the flesh contacting the hook arm of each of the plurality of surgical retractor hooks, thereby retracting the flesh in a lateral direction.

20. The method of claim 19, wherein the tension lines are in operative engagement with a retractor frame, wherein the retractor frame is operable to be situated lateral to a patient.

* * * * *